US011324245B2

(12) United States Patent
Harm

(10) Patent No.: US 11,324,245 B2
(45) Date of Patent: May 10, 2022

(54) BEET JUICE WITH INCREASED INTESTINAL ABSORPTION, ITS MANUFACTURING METHOD AND ITS USE

(71) Applicant: BAERYEO CO., LTD., Jeju-si (KR)

(72) Inventor: Daisik Harm, Jeju-si (KR)

( * ) Notice: Subject to any disclaimer, the term of this patent is extended or adjusted under 35 U.S.C. 154(b) by 0 days.

(21) Appl. No.: 16/626,361

(22) PCT Filed: Jun. 26, 2019

(86) PCT No.: PCT/KR2019/007692
§ 371 (c)(1),
(2) Date: Dec. 24, 2019

(87) PCT Pub. No.: WO2020/009362
PCT Pub. Date: Jan. 9, 2020

(65) Prior Publication Data
US 2021/0329957 A1    Oct. 28, 2021

(30) Foreign Application Priority Data

Jul. 2, 2018 (KR) .................. 10-2018-0076724
Apr. 17, 2019 (KR) .................. 10-2019-0044885

(51) Int. Cl.
| A61K 36/00 | (2006.01) |
| A23L 33/105 | (2016.01) |
| A23L 19/00 | (2016.01) |
| A23L 33/00 | (2016.01) |
| A61P 9/12 | (2006.01) |
| A23B 7/015 | (2006.01) |
| A23L 2/04 | (2006.01) |
| A23L 2/50 | (2006.01) |
| A61K 9/00 | (2006.01) |
| A61K 36/21 | (2006.01) |
| A61K 36/23 | (2006.01) |
| A61K 36/73 | (2006.01) |

(52) U.S. Cl.
CPC ............ *A23L 33/105* (2016.08); *A23B 7/015* (2013.01); *A23L 2/04* (2013.01); *A23L 2/50* (2013.01); *A23L 19/09* (2016.08); *A23L 33/40* (2016.08); *A61K 9/0056* (2013.01); *A61K 36/21* (2013.01); *A61K 36/23* (2013.01); *A61K 36/73* (2013.01); *A61P 9/12* (2018.01); *A23V 2002/00* (2013.01); *A61K 2236/13* (2013.01); *A61K 2236/15* (2013.01); *A61K 2236/37* (2013.01)

(58) Field of Classification Search
CPC ... A23L 2/04; A23L 19/09; A23L 5/21; A61K 2236/13
See application file for complete search history.

(56) References Cited

U.S. PATENT DOCUMENTS

2008/0050498 A1* 2/2008 Sherwood ............ A23C 9/1526
426/583

FOREIGN PATENT DOCUMENTS

| KR | 10-0188553 | 6/1999 |
| KR | 10-2013-0048958 | 5/2013 |
| KR | 10-1293072 | 8/2013 |
| KR | 10-2016-0144034 | 12/2016 |
| KR | 10-2017-0025299 | 3/2017 |

OTHER PUBLICATIONS

English Specification of 10-2017-0025299.
English Specification of 10-2016-0144034.
English Specification of 10-0188553.
English Specification of 10-1293072.
English Specification of 10-2013-0048958.
Ditter A. Hobbs, et al., Blood pressure-lowering effects of beetroot juice and novel beetrootenriched. British Journal of Nutrition, 2012, 108, 2066-2074.
How to prepare a detoxification beet juice, What efficacy of beet juice?, NAVER blog, Mar. 28, 2018., URL: https://blog.naver.com/kmc5apw/221239669637.
English translation of "How to prepare a detoxification beet juice, What efficacy of beet juice?, NAVER blog, Mar. 28, 2018., URL: https://blog.naver.com/kmc5apw/221239669637".

* cited by examiner

*Primary Examiner* — Qiuwen Mi
(74) *Attorney, Agent, or Firm* — Antonio Ha & U.S. Patent, LLC

(57) ABSTRACT

The present invention relates to a beet juice with an increased intestinal absorption rate, a method for manufacturing the beet juice, and use of the same, and more specifically, to a beet juice with an intestinal digestion and absorption rate increased by transforming high-molecular compounds into low-molecular compounds by low-temperature ripening a beet, with the earthy flavor removed by baking the beet, and with the earthy and bitter taste mitigated by adding a carrot juice or apple juice, and an anti-oxidative, or anti-hypertensive, healthy food composition using the beet juice.

3 Claims, 12 Drawing Sheets

BEET JUICE WITH INCREASED INTESTINAL ABSORPTION, ITS MANUFACTURING METHOD AND ITS USE

TECHNICAL FIELD

The present invention relates to a beet juice with increased intestinal absorption and a method and use of producing the beet juice, and more specifically, to a beet juice with intestinal absorption increased by transforming high-molecular compounds in beet into low-molecular compounds by low-temperature ripening, a method for producing the beet juice, and healthy foods for anti-oxidation or anti-hypertensive healthy foods containing the beet juice.

BACKGROUND ART

Beet, also called "red radish," is rich in nutrients. The red color, Betaine, contained in beet enhances muscular strengths and stamina, suppresses cell damage, and shows anti-oxidation effects that may prevent cancer and mitigate inflammation.

Beet also contains a good amount of iron and vitamins which aid in producing red blood cells and clean blood and is thus good for women with dysmenorrhea or menopausal disorder and protects the stomach. Beet is also a good source of dietary fiber which may alleviate constipation.

Beet is typically cooked and eaten or, for preserving nutrients, beet may also be eaten raw as a salad. However, the vegetable's unique bitter taste gets raw eating unwilling and its high-molecular compounds are seldom absorbed.

There are ongoing research efforts to help ones eat raw beetroot without reluctance. For example, Korean Patent No. 10-2017-0025299 discloses a manufacturing method for maintaining the taste and color of beet and minimizing nutrient loss by compressing and ripening, then freeze-drying and powdering beet. Korean Patent Application Publication No. 10-2016-0144034 discloses a method for manufacturing a beet tea that is given a rich taste by ripening and heat-drying a mixture of beet and functional hubs. Korean Patent No. 10-0188553 discloses a method for manufacturing a red beet juice that is allowed to preserve its color and taste by soaking red beet in a vitamin solution, then extracting and filtering, and then mixing the same with an oligo-saccharide, followed by high-temperature pasteurization.

However, the prior art documents merely disclose maintaining the color or taste of beet powder or beverage or allowing people to readily enjoy beet beverages but not how to raise the intestinal absorption of effective nutrients of beet.

The inventors of this application have developed a beet juice with an intestinal absorption increased by transforming high-molecular compounds of beet into low-molecular compounds and with the beet's bitterness and earthy flavor suppressed. The inventors have also verified that a beet juice with an increased intestinal absorption shows superior anti-oxidation and blood pressure dropping effects.

DETAILED DESCRIPTION OF THE INVENTION

Technical Problems

An object of the present invention is to provide a beet juice with an intestinal digestion and absorption rate increased by transforming high-molecular compounds in beet into low-molecular compounds via low-temperature ripening.

Another object of the present invention is to provide a method of manufacturing a beet juice with an intestinal absorption increased by transforming high-molecular compounds in beet into low-molecular compounds via low-temperature ripening.

Still another object of the present invention is to provide an anti-oxidative healthy food containing a low temperature-ripen beet juice with an intestinal digestion and absorption rate increased by transforming high-molecular compounds in beet into low-molecular compounds by low-temperature ripening.

Yet still another object of the present invention is to provide a healthy food for dropping blood pressure, which contains a low temperature-ripen beet juice with an intestinal digestion and absorption rate increased by transforming high-molecular compounds in beet into low-molecular compounds by low-temperature ripening.

Means to Address the Problems

To achieve the above objectives, according to the present invention, there is provided a method for manufacturing a beet juice, including a first step of washing a beet and heating the washed beet at a temperature ranging from 200° C. to 300° C. for 30 seconds to one minute, a second step of juicing the baked beet, a third step of low-temperature ripening the beet juice at a temperature ranging from 0° C. to 10° C. for three days to four days, and a fourth step of mixing the low-temperature ripen beet juice with a carrot juice, an apple juice, and a lemon juice.

Further, according to the present invention, there is provided a beet juice beverage with an intestinal digestion and absorption rate, which includes a beet juice obtained by baking, juicing, and low-temperature ripening a peeled beet, a carrot juice, an apple juice, and a lemon juice.

Further, according to the present invention, there is provided an anti-oxidative healthy food which includes a low temperature-ripen beet juice obtained by baking, juicing, and low-temperature ripening a peeled beet, a carrot juice, and an apple juice.

Further, according to the present invention, there is provided a use, as an anti-oxidative healthy food, of a low temperature-ripen beet juice obtained by baking, juicing, and low-temperature ripening a peeled beet, a carrot juice, and an apple juice.

Further, according to the present invention, there is provided an anti-hypertensive healthy food which includes a low temperature-ripen beet juice obtained by baking, juicing, and low-temperature ripening a peeled beet, a carrot juice, and an apple juice.

Further, according to the present invention, there is provided a use, as an anti-hypertensive healthy food, of a low temperature-ripen beet juice obtained by baking, juicing, and low-temperature ripening a peeled beet, a carrot juice, and an apple juice.

Effects of the Invention

The present invention may remove earthy smell via baking beet in manufacturing a beet juice, increasing the intestinal digestion and absorption rate by transforming high-molecular compounds in beet into low-molecular compounds by low-temperature ripening, and manufacture a beet juice which is allowed to be sweet and have the bitter and earthy smell reduced by mixing with a carrot juice, apple juice, and/or lemon juice.

Further, according to the present invention, the beet juice contains polyphenols and has anti-oxidation activities, such as DPPH radical scavenging activity and ABTS radical scavenging activity. From animal experimentation, it has been verified that the beet juice of the present invention, when orally administered, may drop blood pressure, increase nitrite and decrease the MDA in blood, and enhance blood vessel reactions to acetylcholine without noticeable changes in the organ indexes, thus mitigating high-blood pressure. Thus, the beet juice of the present invention may be useful for anti-oxidative or anti-hypertensive healthy foods.

BEST MODE FOR PRACTICING THE PRESENT INVENTION

Figure 1:
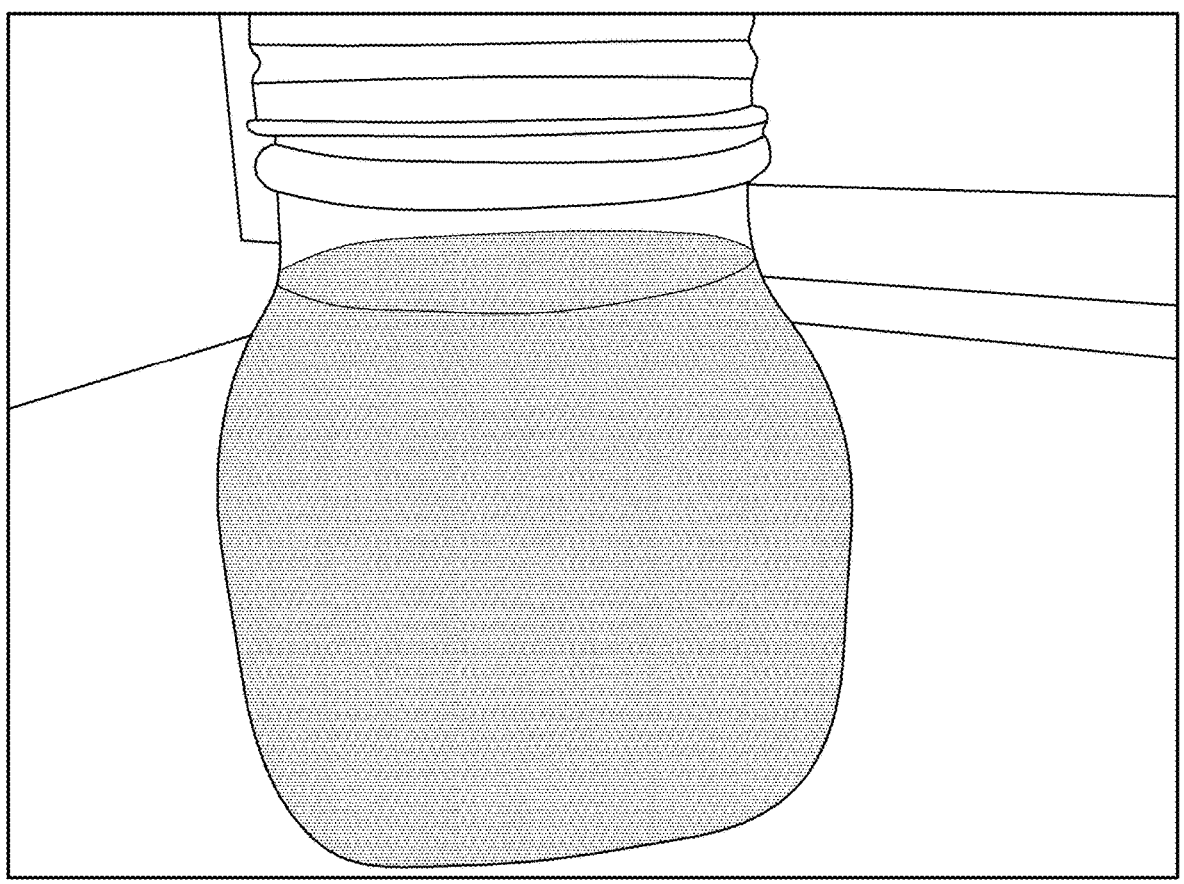
FIG. 1 illustrates a beet juice manufactured according to the present invention.

Hereinafter, the present invention is described in detail. Known configurations or functions relevant to the present invention may be omitted from the detailed description of the present invention.

The terms used in the specification and the claims should not be interpreted as limited to their typical or dictionary meanings but should rather be interpreted as complying with the technical spirits of the present invention.

The embodiments described herein and the configurations shown in the drawings are preferred embodiments of the present invention but do not represent all of the technical spirits of the present invention and, thus, various equivalents or changes may be made thereto as of the time of filing the instant application.

A method for manufacturing a beet juice according to the present invention is described below in detail.

According to the present invention, a method for manufacturing a beet juice includes a first step of washing a beet and baking the washed beet at a temperature ranging from 200° C. to 300° C. for 30 seconds to one minute, a second step of juicing the baked beet, a third step of low-temperature ripening the beet juice at a temperature ranging from 0° C. to 10° C. for three days to four days, and a fourth step of mixing the low-temperature ripen beet juice with a carrot juice, an apple juice, and a lemon juice.

First, a beet is washed and baked (the first step).

In the first step, it is preferable to peel off the beet and then bake the peeled beet at a temperature ranging from 200° C. to 300° C. for 30 seconds to one minute.

At this time, if the baking temperature is lower than the temperature range or the baking time is shorter than the above time, the beet may be unevenly baked and may thus lose its rich taste. If the baking temperature is higher than the temperature range or the baking time is longer than the above time, the yeast or enzymes in the beet may perish, causing the beet to lose its efficacy.

Next, the baked beet is juiced (the second step).

The second step may be performed by a juicer.

The juiced beet is low temperature-ripen (the third step).

The third step is performed as low-temperature ripening preferably in a storage container whose temperature ranges from 0° C. to 10° C., or more preferably in a storage container whose temperature ranges from 4° C. to 5° C.

The low-temperature ripening is preferably performed for three days to four days.

In this case, if the ripening temperature is less than 0° C., which is too low, the juiced beet may be frozen to cause ripening impossible. If the ripening temperature exceeds 10° C., the juiced beet may become too viscous to drink.

If the ripening is less than three days, the beet remains with its earthy or bitter taste and is not good for drinking. If the ripening is longer than four days, the color and taste of the beet juice may be easily changed.

Next, a carrot juice, an apple juice, and a lemon juice are mixed with the low temperature-ripen beet juice (the fourth step).

In the fourth step, the low temperature-ripen beet juice, the carrot juice, the apple juice, and the lemon juice are mixed preferably in a ratio of 20 to 40 parts by weight:10 to 20 parts by weight:30 to 50 parts by weight:0.5 to 1 parts by weight.

The carrot juice, apple juice, and lemon juice are intended for mitigating the bitter and earthy smell of beet. If the carrot juice, apple juice, or lemon juice is added less than the above content, the bitter and earthy smell of beet remains, causing it reluctant to drink the beet juice. If the carrot juice, apple juice, or lemon juice is added more than the above content, the carrot, apple, or lemon may be a dominant taste so that the beet juice may lose its efficacy.

In the fourth step, it is preferable to wash and then juice the carrot, apple, and lemon.

At this time, juicing the carrot, apple, and lemon may be performed by a juicer.

The method of the present invention may further include the steps of pasteurizing and packaging the mixture prepared in the fourth step.

The pasteurization step is preferably non-heating, low-temperature pasteurization at a temperature not more than 40° C. using a pulsed electric field (PEF) device.

Since the yeast and enzymes in the beet may perish, starting at 40° C. and fully at 60° C., low-temperature pasteurization of 40° C. or less is preferable.

The present invention also provides a beet juice beverage with an enhanced intestinal digestion and absorption rate, which contains a beet juice obtained by baking, juicing, and low-temperature ripening a peeled beet, a carrot juice, an apple juice, and a lemon juice.

The beet juice beverage has a dark red or wine color which is the color of red beet and is non-sticky liquid which is easy to package in a glass container.

In the beet juice beverage, the high-molecular compounds are transformed into low-molecular compounds by low-temperature ripening. The beet juice beverage, when drunken, leaves no red color, which is the unique red color of beet, in the feces and shows a superior intestinal digestion and absorption rate. The earthy smell of beet may be removed by the baking step. The bitter and earthy smell of beet may also be mitigated by adding the carrot juice, apple juice, and lemon juice to allow it appropriate to drink.

Further, the present invention also provides a beet juice beverage with an intestinal digestion and absorption rate, which contains a beet juice obtained by baking, juicing, and low-temperature ripening a peeled beet and an apple juice.

Preferably, the low temperature-ripen beet juice and the apple juice are mixed together in a weight ratio of 3:7.

In the beet juice beverage, it is preferable to add or mix any one or more of a carrot juice or a lemon juice.

In this case, the low temperature-ripen beet juice, the carrot juice, and the apple juice are mixed preferably in a weight ratio of 2.0 to 3.0:1.5 to 2.5:5.0 to 6.0, more preferably in a weight ratio of 2.5:2:5.5.

The present invention also provides an anti-oxidative healthy food including a low temperature-ripen beet juice obtained by baking, juicing, and low-temperature ripening a peeled beet, a carrot juice, and an apple juice.

In the anti-oxidative healthy food, the low temperature-ripen beet juice, the carrot juice, and the apple juice are mixed preferably in a weight ratio of 2.0 to 3.0:1.5 to 2.5:5.0 to 6.0, more preferably in a weight ratio of 2.5:2:5.5.

In this case, if the apple juice is added in 50% or less of the total weight, the beet juice may start to gel. Thus, a proper mixing proportion of the apple juice is preferable to prevent the beet juice from gelling.

Preferably, the anti-oxidative healthy food may further include a lemon juice to add taste and flavor.

The healthy food may be a health functional food or a dietary supplement.

The present invention also provides an anti-oxidative healthy food including a low temperature-ripen beet juice obtained by baking, juicing, and low-temperature ripening a peeled beet and an apple juice.

In the anti-oxidative healthy food, the low temperature-ripen beet juice and the apple juice are mixed together preferably in a weight ratio of 3:7.

The healthy food may be a health functional food or a dietary supplement.

The present invention also provides an anti-hypertensive healthy food including a low temperature-ripen beet juice obtained by baking, juicing, and low-temperature ripening a peeled beet, a carrot juice, and an apple juice.

In the anti-hypertensive healthy food, the low temperature-ripen beet juice, the carrot juice, and the apple juice are mixed together preferably in a weight ratio of 2.0 to 3.0:1.5 to 2.5:5.0 to 6.0, more preferably in a weight ratio of 2.5:2:5.5.

In this case, if the apple juice is added in 50% or less of the total weight, the beet juice may start to gel. To prevent the beet juice from gelling, an appropriate mixing proportion of the apple juice is preferable.

Preferably, the anti-hypertensive healthy food may further include a lemon juice to add taste and flavor.

The healthy food may be a health functional food or a dietary supplement.

The present invention also provides an anti-hypertensive healthy food including a low temperature-ripen beet juice obtained by baking, juicing, and low-temperature ripening a peeled beet and an apple juice.

In the anti-hypertensive healthy food, the low temperature-ripen beet juice and the apple juice are mixed together preferably in a weight ratio of 3:7.

The healthy food may be a health functional food or a dietary supplement.

The healthy food of the present invention may add the beet juice of the present invention as it is, or add other foods or food ingredients and may be properly used in a typical manner.

In the healthy food of the present invention, 50 to 90 parts by weight of the beet juice may be included relative to 100 parts by weight of all the healthy food composition.

The healthy food of the present invention is not limited to a specific kind. Example foods which my contain the beet juice may include beverages, alcohol drinks, dairy products, meats, noodles, snacks, ice creams, or any typical kinds of healthy foods.

The healthy food of the present invention may add various flavors or sweeteners as do typical beverages. The healthy food of the present invention may add various nutritional supplements, vitamins, electrolytes, flavors, colorants, pectic acid and its salts, alginic acid and its salts, organic acids, protective colloid thickeners, pH adjusters, stabilizers, preservative, glycerin, alcohols, and/or carbonators used in sodas, or other various kinds of pulp. The components may be used independently or in combinations thereof. Although the proportions of the additives are not critical, they are typically selected in a range from 0.01 parts by weight to 0.1 parts by weight relative to 100 parts by weight of the entire healthy food composition.

Embodiments of the present invention are described below in greater detail. The embodiments are intended for more specifically describing the present invention and it will be apparent to one of ordinary skill in the art that the scope of the present invention is not limited to or by the embodiments.

<Embodiment 1> Beet Juice Manufacture 1

1 Kg of beet was washed with clean water, then peeled off and baked at 200° C. for one minute, and then juiced by a juicer into a beet juice. The beet juice was subjected to low-temperature ripening in a 5° C. storage container for three days, and then mixed with a carrot juice, an apple juice, and a lemon juice. The low temperature-ripen beet juice, the carrot juice, the apple juice, and the lemon juice were mixed in a weight % ratio of 40:20:39:1.

The resultant mixture was non-heating, low-temperature pasteurized by a pulsed electric field (PEF) device.

<Embodiment 2> Beet Juice Manufacture 2

The same process as in embodiment 1 was performed except that the beet was baked at 250° C. for 30 seconds.

<Embodiment 3> Beet Juice Manufacture 3

The same process as in embodiment 1 was performed except that the beet juice was subjected to low-temperature ripening in a 10° C. storage container for three days.

<Embodiment 4> Beet Juice Manufacture 4

The same process as in embodiment 1 was performed except that the beet juice, the carrot juice, the apple juice, and the lemon juice were mixed in a weight % ratio of 30:20:49.5:0.5.

<Comparative Example 1> Manufacture without Baking Beet

The same process as in embodiment 1 was performed except that the beet was not baked.

<Comparative Example 2> Manufacture Under a Different Beet Baking Condition

The same process as in embodiment 1 was performed except that the beet was baked at 250° C. for two minutes.

<Comparative Example 3> Manufacture without Low-Temperature Ripening

The same process as in embodiment 1 was performed except that no low-temperature ripening was performed.

<Comparative Example 4> Manufacture Under a Different Ripening Condition

The same process as in embodiment 1 was performed except that the beet juice was subjected to ripening at room temperature (20° C. to 25° C.) for three days.

<Comparative Example 5> Manufacture Under a Different Mixing Condition

The same process as in embodiment 1 was performed except that the beet juice, the carrot juice, the apple juice, and the lemon juice were mixed in a weight % ratio of 50:19:30:1.

<Comparative Example 6> Manufacture Under a Different Mixing Condition

The same process as in embodiment 1 was performed except that the beet juice, the carrot juice, the apple juice, and the lemon juice were mixed in a weight % ratio of 15:25:55:5.

<Comparative Example 7> Manufacture Under a Different Pasteurization Condition

The same process as in embodiment 1 was performed except that pasteurization was performed at 70° C. to 80° C. using a high-temperature pasteurizer.

<Experimental Example 1> Sensory Testing

Sensory testing was performed to figure out the taste, flavor and overall preference on the beet juices manufactured by embodiments 1 to 4 and comparative examples 1 to 7.

20 adult males (five in their twenties, five in their thirties, five in their forties, and five in their fifties) and 20 adult females (five in their twenties, five in their thirties, five in their forties, and five in their fifties) were selected and trained for the test to score each beet juice on four test items: taste, flavor, mouthfeel, and overall preference, based on the following standard.

Very good: 10
Good: 8
So so: 4
Bad: 4
Very bad: 2

The results are shown in Table 1 below:

TABLE 1

|  | taste | flavor | mouthfeel | preference |
| --- | --- | --- | --- | --- |
| Embodiment 1 | 9.2 | 9.5 | 9.0 | 9.3 |
| Embodiment 2 | 9.0 | 9.3 | 8.5 | 9.3 |
| Embodiment 3 | 9.2 | 9.1 | 8.9 | 9.0 |
| Embodiment 4 | 9.2 | 9.5 | 8.3 | 8.9 |
| Comparative example 1 | 5.8 | 4.2 | 6.2 | 5.5 |
| Comparative example 2 | 5.9 | 4.1 | 6.0 | 5.1 |
| Comparative example 3 | 5.1 | 4.4 | 5.8 | 4.8 |
| Comparative example 4 | 5.7 | 4.0 | 6.0 | 4.7 |
| Comparative example 5 | 5.0 | 4.0 | 5.9 | 4.9 |
| Comparative example 6 | 5.2 | 4.0 | 6.0 | 4.9 |
| Comparative example 7 | 5.5 | 4.0 | 6.0 | 5.3 |

As a result of evaluation on taste, the beet juices manufactured by embodiments 1 to 4 tasted savory, with the beet smells gone by the baking step, and delivered a better flavor by adding adequate amounts of carrot juice, apple juice, and lemon juice. Further, the beet juices remained at a proper low temperature while manufactured, thus preventing the yeast and enzymes from perishing.

In contrast, the beet juice manufactured by comparative example 1, which has no baking step, was left with the earthy and bitter taste of beet, and even soil smells. When baked for a long time as in comparative example 2, the beet juices left no beet yeast and enzymes and smelled bad. Under the ripening conditions of comparative examples 3 and 4, the high-molecular compounds which are not digested well remained and were thus scored low in light of preference. The different mixing conditions as in comparative examples 5 and 6 left the strong earthy and bitter taste of beet in the beet juices. The beet juice manufactured by comparative example 7 failed to preserve the beet yeast and enzymes due to the high-temperature pasteurization and showed a poor mouthfeel.

<Experimental Example 2> Identify Digestion and Absorption Rate

A clinical test was carried out to figure out the digestion and absorption rates of beet juices manufactured by embodiments 1 to 4 and comparative examples 1 to 7.

To reduce significant differences and constitute testers of similar genders and ages, 44 testers in total participated in the test; two males and two females in their thirties for each experimental group, i.e., each of embodiments 1 to 4 and comparative examples 1 to 7.

They were stopped from eating other fruits or drinking other juices from three days before the date of test until the test was ended and were requested to drink a cup of beet juice (250 ml) of each experimental group daily for one week. The intestinal digestion and absorption rate was evaluated on three items of the one-week period: the state of feces during the one-week period; regular bowel movement; and stomach comfortability, which were scored based on the following standard. The feces were observed with the naked eye.

Very good: 10

Good: 8

Normal: 6

Bad: 4

Very bad: 2

The results are shown in Table 2 below.

|  | State of feces | Color of feces | Regular bowel movement | Stomach comfortability |
| --- | --- | --- | --- | --- |
| Embodiment 1 | 8.2 | No big difference from normal stool color | 8.5 | 8.6 |
| Embodiment 2 | 8.0 | | 8.1 | 8.4 |
| Embodiment 3 | 8.0 | | 8.2 | 8.5 |
| Embodiment 4 | 8.1 | | 8.4 | 8.3 |
| Comparative example 1 | 6.8 | Red stool | 6.1 | 6.5 |
| Comparative example 2 | 6.5 | | 5.4 | 5.2 |
| Comparative example 3 | 6.3 | Dark red stool | 5.1 | 5.0 |
| Comparative example 4 | 6.4 | | 5.2 | 5.3 |
| Comparative example 5 | 6.6 | Light red stool | 5.7 | 5.6 |
| Comparative example 6 | 6.5 | | 5.8 | 5.6 |
| Comparative example 7 | 6.4 | | 5.9 | 5.8 |

As a result of the clinical test, it was identified that the testers who drank the beet juices manufactured by embodiments 1 to 4 mostly showed 8.0 (Good) or more for the state of feces, regular bowel movement, and stomach comfortability and no or little difference in stool color from normal stools.

In contrast, when drinking the beet juices manufactured by comparative examples 1 to 2, the stool color was not good, the regular bowel movement was normal, and so was the stomach comfortability, and the stool color was reddish. After drinking the beet juices of comparative examples 3 and 4, the testers complained about indigestion, and the state of feces, regular bowel movement, and stomach comfortability all were not good, with the stool color identified to be mostly dark red.

Comparative examples 5 and 6 resulted in a poor taste and mouthfeel, thus making the state of feces, regular bowel movement, and stomach comfortability scoring low, and so did comparative example 7. After drinking the beet juices of comparative examples 5 to 7, the testers were identified to turn the stool light red.

<Experimental Example 3> Analysis of Total Polyphenol Content

<3-1> Prepare for Samples

As sample 2 (S2), a beet juice with an increased intestinal absorption rate was prepared by mixing a low temperature-ripen beet juice, a carrot juice, and an apple juice in a weight ratio of 2.5:2:5.5 as in the method of embodiment 1 above.

As sample 1 (S1), a pure beet juice was prepared by juicing a beet.

As sample 3 (S3), a diluted beet juice was prepared by diluting two times sample 2 with distilled water.

<3-2> Measure Total Polyphenol Content

Polyphenols are chemicals discovered from plants and, with flavonoids, catechin, and tannins as their major components, polyphenols are known to have anti-oxidation, anti-cancer, and anti-hypertensive effects.

The total polyphenol content was measured using the Folin-Deni method. 100 µl of Folin-ciocalteu's phenol reagent was added to 1 ml of each sample 1, 2, and 3 and was left at room temperature for five minutes for reaction. Then, 700 µl of distilled water and 200 µl of $Na_2CO_3$ solution (7%, w/v) were added to the mixture and were left at room temperature for one hour for reaction. After reaction, the absorbance was measured, and the total polyphenol content for the extract was shown using a standard calibration curve created using the gallic acid.

Figure 2:
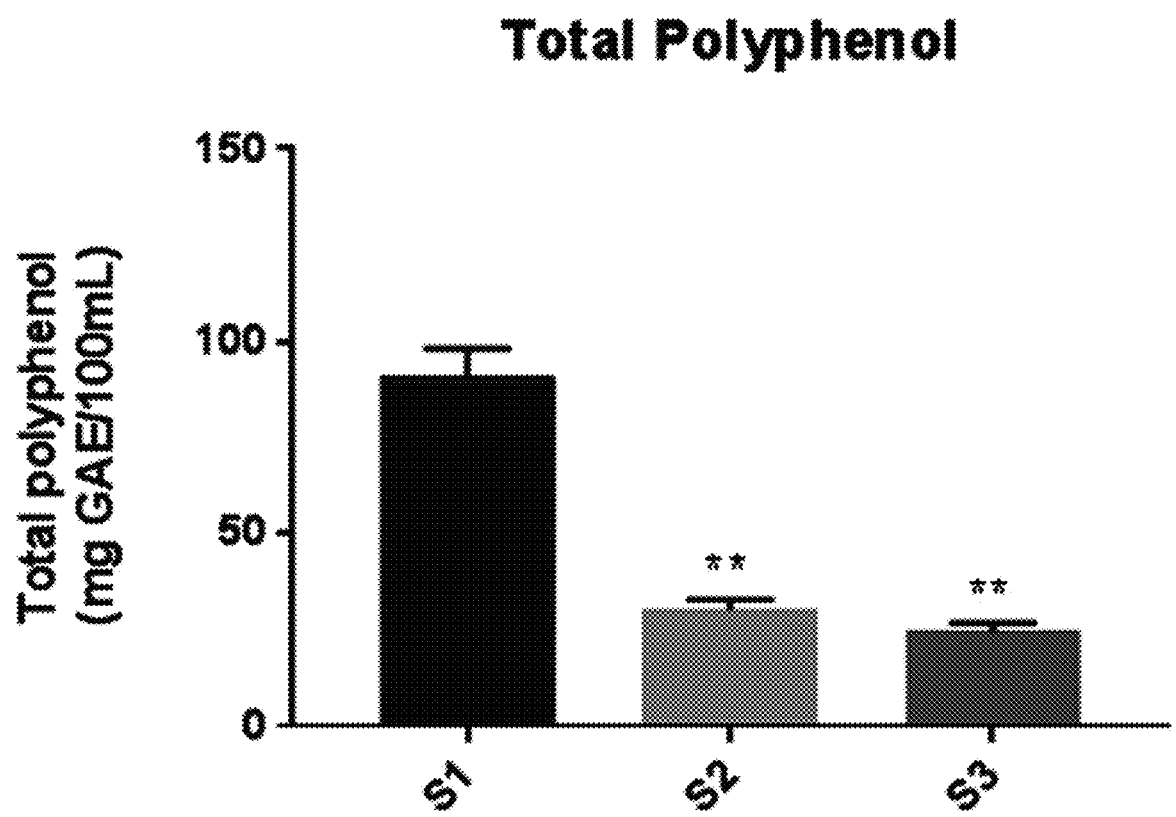
FIG. 2 is a graph illustrating a result of measuring the total polyphenols contained in a beet juice manufactured according to the present invention.

As a result, the total polyphenol content was identified to be high in samples 2 and 3 as shown in FIG. 2 (FIG. 2).

<Experimental Example 4> Analysis of DPPH Radical Scavenging Activity

<4-1> Prepare for Samples

Sample 1 (S1), sample 2 (S2), and sample 3 (S3) were prepared as in embodiment 3-1.

<4-2> Measure DPPH Radical Scavenging Activity

DPPH radical scavenging activity is a relatively simple anti-oxidation measuring method which measures the anti-oxidation activity based on the principle that the DPPH receives electrons or hydrogen from phenol compounds to thereby reduce into DPPH-H so that the violet is decolored.

The Blois method was adopted for the DPPH radical scavenging activity test. 0.2 mM of DPPH was prepared and mixed with each sample and was left at room temperature for 10 minutes. Then, the absorbance was measured at 517 nm using the ELASA reader SpectraMax® M3 multi-mode microplate reader (Molecular Devices, Sunnyvale, Calif., USA). The concentration (SC50) shown when the absorbance of DPPH is reduced to 50% was marked, and each sample was tested repeatedly three times, and the mean value was obtained. At this time, vitamin C was used as a control group.

Figure 3:
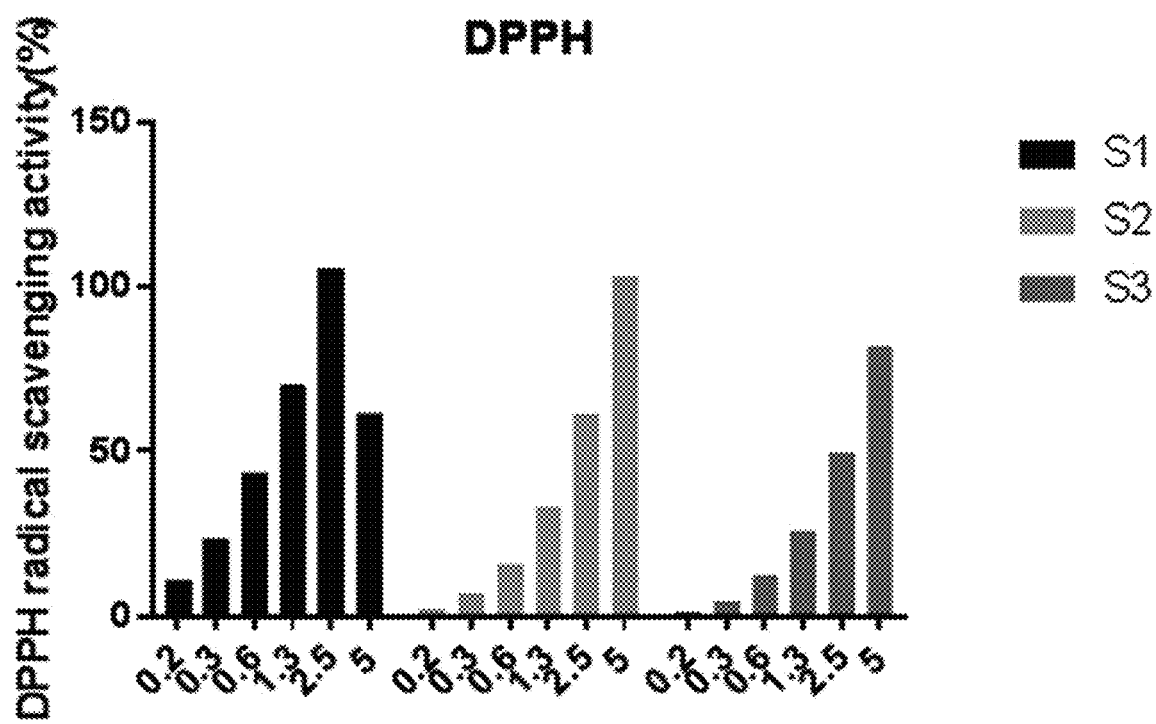
FIG. 3 is a graph illustrating a result of measuring the DPPH radical scavenging activity of a beet juice manufactured according to the present invention.

As a result, as shown in FIG. 3, samples 2 and 3 were identified to have a superior DPPH radical scavenging activity (FIG. 3).

<Experimental Example 5> Analysis of ABTS Radical Scavenging Activity

Sample 1 (S1), sample 2 (S2), and sample 3 (S3) were prepared as in embodiment 3-1 above.

<5-2> Measure ABTS Radical Scavenging Activity

For ABTS radical scavenging activity, 7.4 mM of ABTS and 2.6 mM of potassium persulfate were mixed and then left for 15 hours, with light blocked, forming radicals. Then, the solution was prepared to have an absorbance of 0.70±0.02 at 734 nm. 20 µl of each sample was added to the 180 µl ABTS solution and then left at room temperature for 15 minutes, and then the absorbance at 734 nm was measured. The ABTS radical scavenging activity was represented in percentage for the absorbance difference between the group with the sample solution added and the group with no sample solution added.

Figure 4:
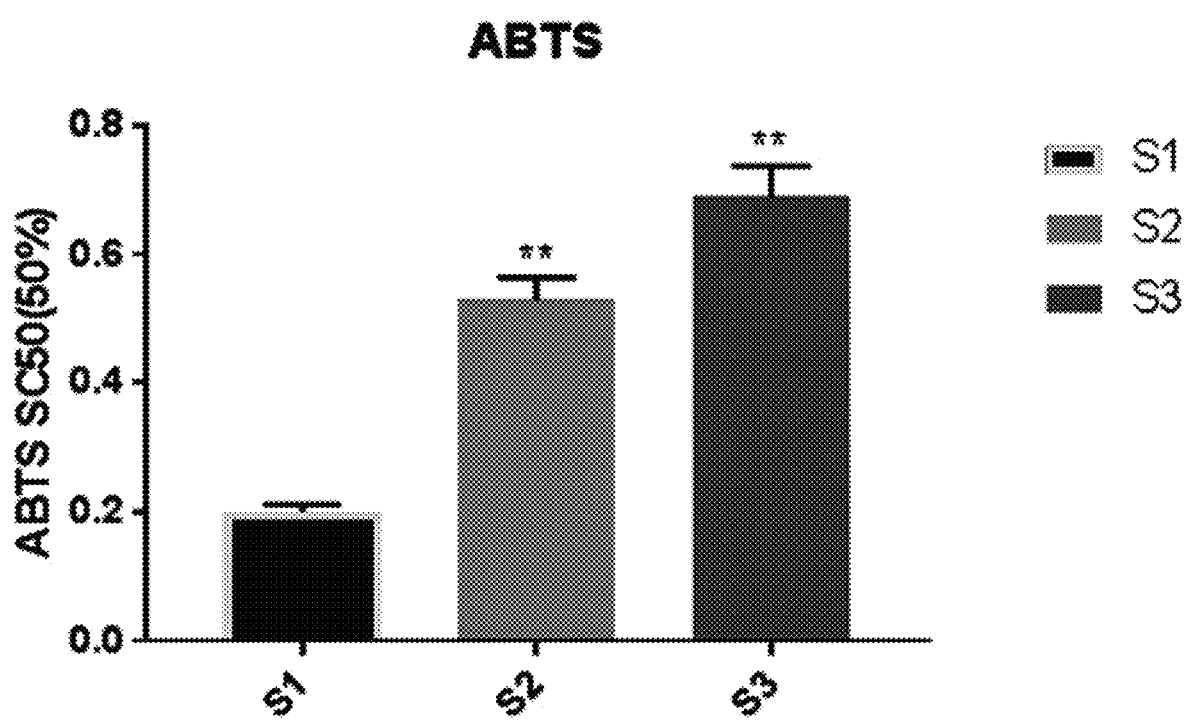
FIG. 4 is a graph illustrating a result of measuring the ABTS radical scavenging activity of a beet juice manufactured according to the present invention.

As a result, as shown in FIG. 4, samples 2 and 3 were identified to have a superior ABTS radical scavenging activity (FIG. 4).

<Experimental Example 6> Analysis of Anti-Oxidation Activity by FRAP Method

<6-1> Prepare Samples

Sample 1 (S1), sample 2 (S2), and sample 3 (S3) were prepared as in embodiment 3-1.

<6-2> Measure Anti-Oxidation Activity by FRAP Method

The FRAP method measures the anti-oxidation activity by measuring variations in absorbance that occur when ferric tripyridyltriazine ($Fe^{3+}$) is reduced into ferrous tripyridyltriazine ($Fe^{2+}$) by an antioxidant at low pH.

The anti-oxidation activity by the ferric reducing antioxidant power (FRAP) method was performed by the Benzie and Strain method. 300 mM of acetate buffer (pH 3.6), a 40 mM HCl solution in which 10 mM of TPTZ (2,4,6-tripyridyl-s-triazine) was dissolved, and 20 mM $FeCl_3.6H_2O$ were mixed in a ratio of 10:1:1 (v/v/v), and the mixture was used as a FRAP base solution. 40 µl of each sample, 100 µl of the FRAP base solution, and 200 µl of distilled water were sequentially mixed in a 96-well plate and left for reaction at 37° C. for four minutes, and then the absorbance was measured at 593 nm. Each sample was tested repeatedly three times and was analyzed using a standard calibration curve obtained using $FeSO_4.7H_2O$ as a standard material.

Figure 5:
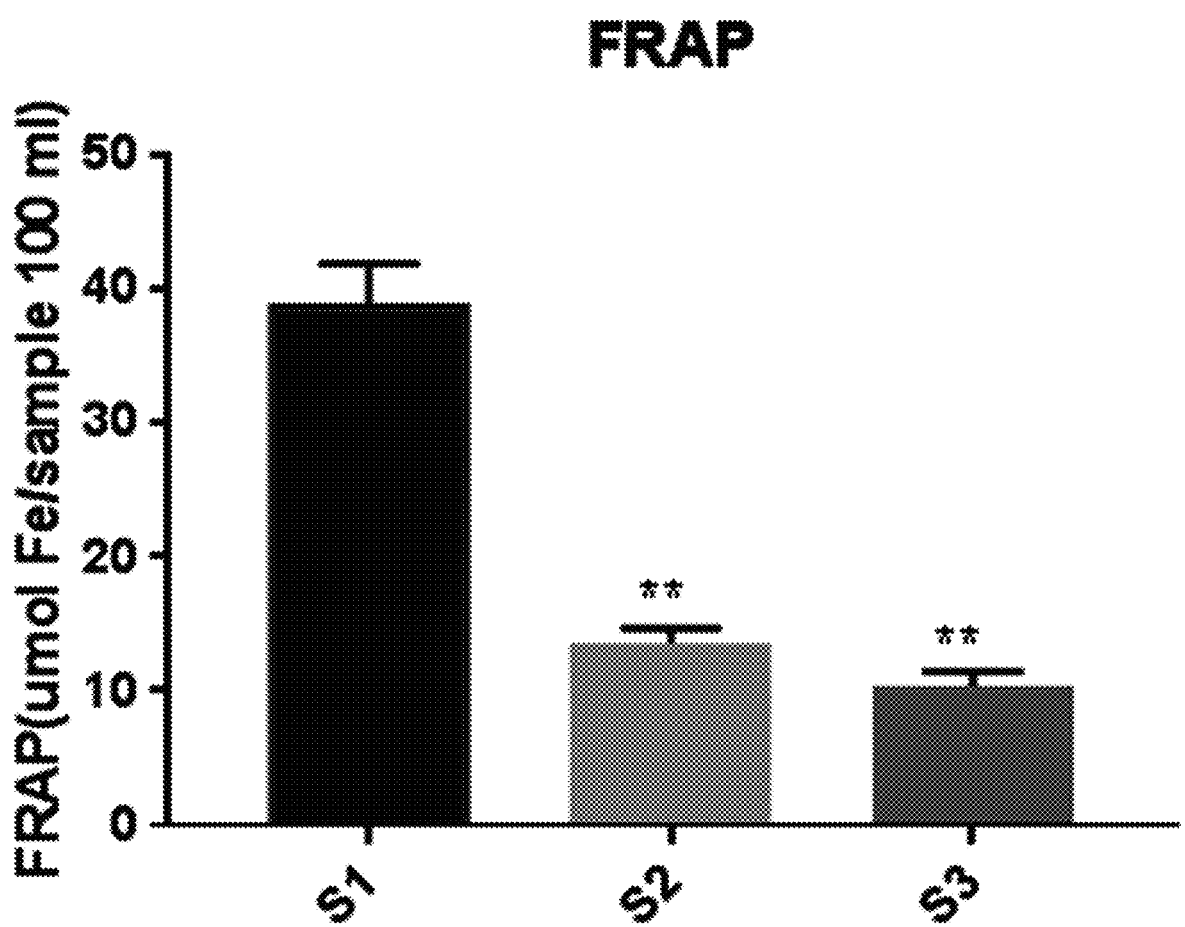
FIG. 5 is a graph illustrating a result of measuring anti-oxidation activity by an FRAP method for a beet juice manufactured according to the present invention.

As a result, as shown in FIG. 5, samples 2 and 3 were identified to have a superior anti-oxidation activity (FIG. 5).

TABLE 3

| Sample | Total polyphenol(mg GAE/100 mL) | DPPH($SC_{50}$, %) | ABTS(SC50, %) | FRAP(umol Fe2/sample ml) |
|---|---|---|---|---|
| 1 | 90.78 ± 7.46 | 0.95 ± 0.06 | 0.2 ± 0.011 | 38.88 ± 2.99 |
| 9 | 30.28 ± 2.52 | 2.01 ± 0.15 | 0.53 ± 0.034 | 13.62 ± 1.06 |
| 3 | 24.66 ± 2.11 | 2.51 ± 0.21 | 0.69 ± 0.047 | 10.44 ± 0.98 |

<Experimental Example 7> Analysis of Betanin

<7-1> Prepare Samples

Sample 1 (S1), sample 2 (S2), and sample 3 (S3) were prepared as in embodiment 3-1 above.

<7-2> Measure Betanin Content

The betanin analysis was performed using 1200 series HPLC (Agilent Technologies, CA, USA) equipped with Synergi 4µ POLAR-RP 80A column (250×4.6 mm, 4 µm Phenomenex). Analysis conditions were 538 nm of detection wavelength, 1.0 ml/min of flow rate, and 35° C. of column temperature. 20.0 µl of the sample was injected using an automatic injector. As a mobile phase solvent, solvent A [water:formic acid, (99:1, v/v) and solvent B (acetonitrile, CH3CN) were used. The solvent concentration gradient was executed based on solvent B, and an analysis time of 25 minutes in total were consumed. Starting with 0%, solvent B was increased to 20% at 15 minutes at 15 minutes, then to 40% at 20 minutes, and was then sharply reduced to 0% at 20.1 minutes and then maintained at 0% to 25 minutes. As betanin, which is an external standard material, has the same retention time (RT), each analyzed component was identified, and the peak area of each betanin component was compared and quantified relative to the HPLC peak area.

Figure 6:
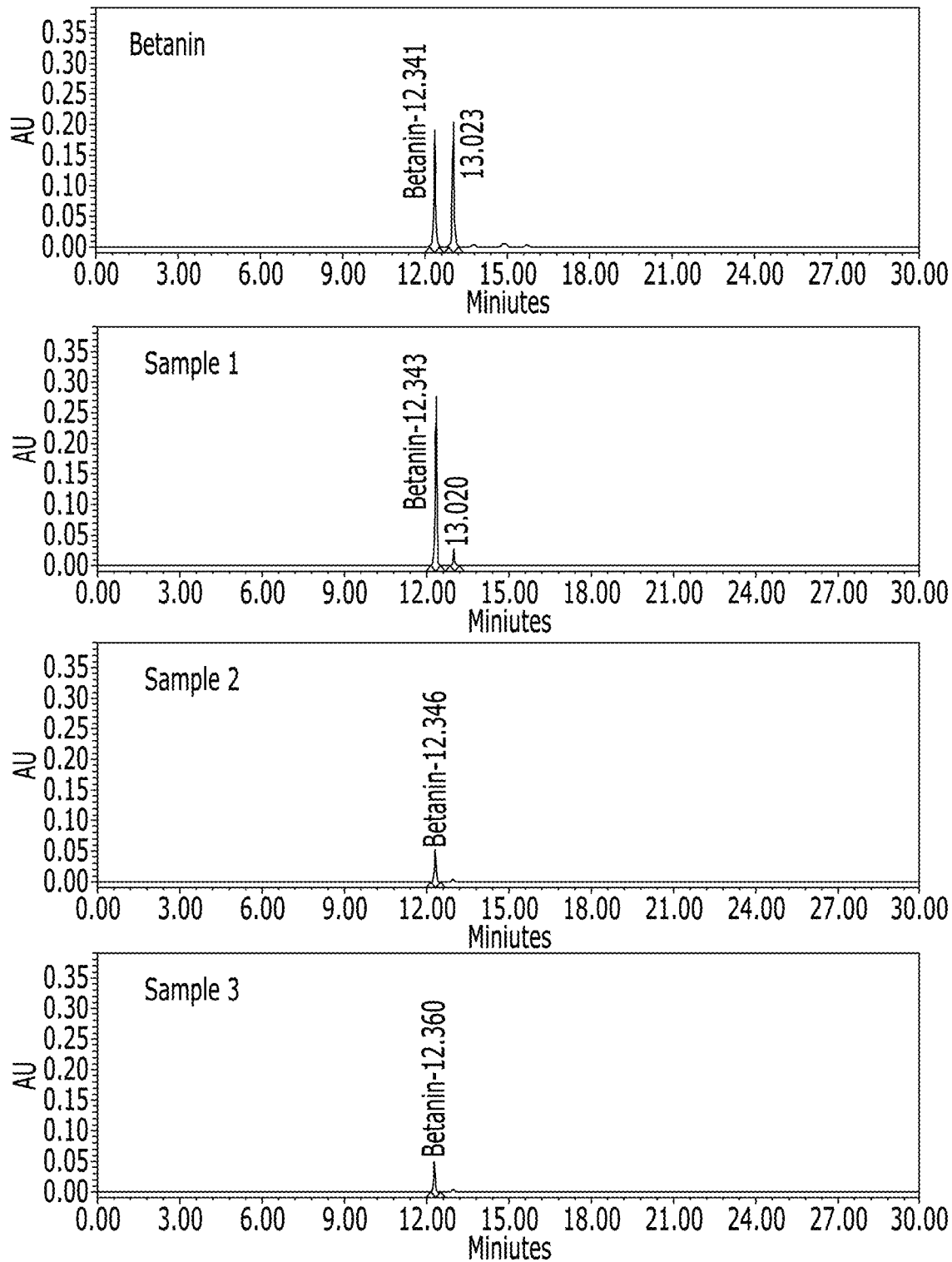
FIG. 6 is a graph illustrating a result of measuring the content of betanin in a beet juice manufactured according to the present invention.

As a result, as shown in FIG. 6, samples 2 and 3 were identified to have a high betanin content (FIG. 6).

<Experimental Example 8> Evaluate Anti-Hypertensive Efficacy in Hypertensive Model Animals <8-1> Prepare Experimental Animals As experimental animals, 24 weeks old female spontaneously hypertensive rats (SHRs) were used. The breeding environment for the experimental animals was a temperature of 23±2° C. and a relative moisture of 50±10%, and the light-dark cycle was adjusted every 12 hours (lighting time: 08:00 to 20:00). All the animal experiments were performed under the authorization by the Animal Care and Use Committee, Jeju National University (Authorization No.: 2018-0053).

When administered repeatedly, the experimental groups were as follows:
Group 1: SHR (drinking water, ad libitum)
Group 2: SHR+Sample 1 (30 ml/day)
Group 3: SHR+Sample 3 (30 ml/day)
Group 4: SHR+Sample 2 (30 ml/day)

<8-2> Measure Variations in Blood Pressure after Orally Administered Once

Each sample was orally administered once to one SHR and variations in blood pressure were observed for 24 hours. The experimental groups were as follows:
Group 1: SHR+D.W. (0.6 ml/rat, p.o.)
Group 2: SHR+Sample 1 (0.6 ml/rat, p.o.)
Group 3: SHR+Sample 2 (0.6 ml/rat, p.o.)
Group 4: SHR+betanin (50 mg/kg, p.o.)

The blood pressure was measured using CODA non-invasive blood pressure system (Kent Scientific, Torrington, Conn.). The temperature of the experimental animal's tail before blood pressure measurement was maintained at 32° C. to 35° C., and blood pressure measurement was performed in a stabilized state. The mean blood pressure of the SHR was 177 mmHg to 182 mmHg.

Figure 7:
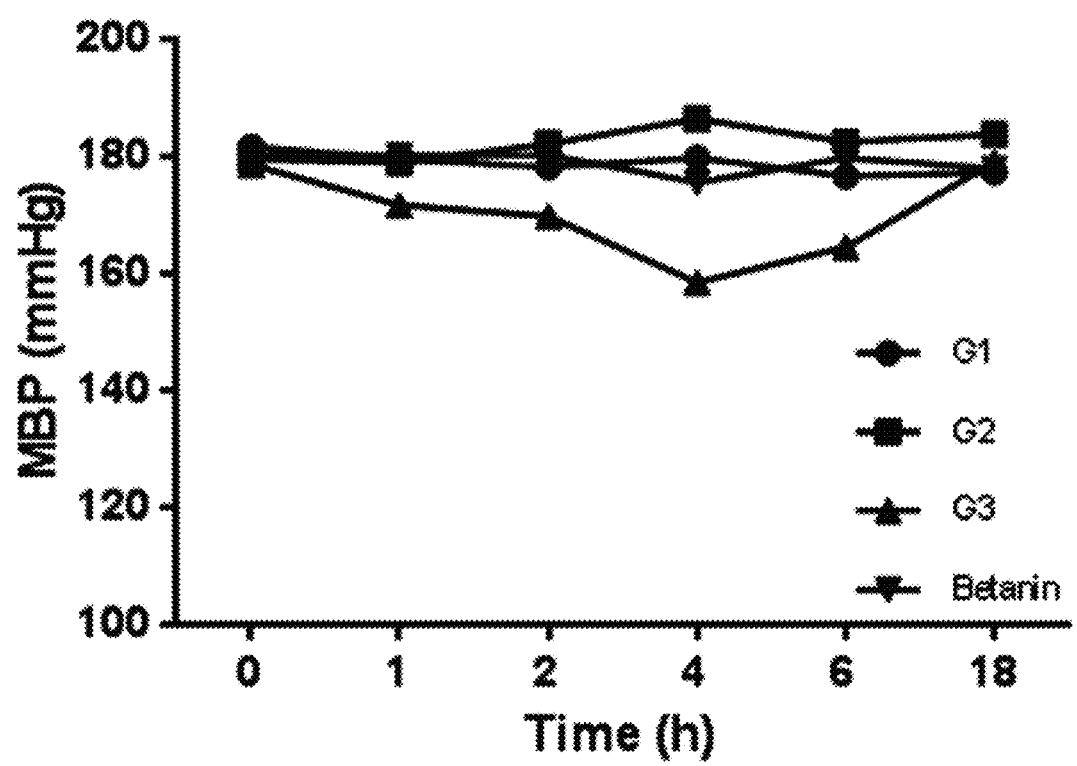
FIG. 7 is a graph illustrating variations in blood pressure after a beet juice manufactured according to the present invention is orally administered once in an animal experiment.

The results are as shown in FIG. 7 (FIG. 7). In the case of sample 2, gradual blood pressure drops were observed within four hours after administered and, thereafter, the blood pressure returned to the original level. In contrast, when sample 1 was administered, a timid blood pressure rise was shown and, when betanin was administered, no difference was found from the control group.

<8-3> Measure Variations in Blood Pressure after Orally Administered Repeatedly

The experimental animals were divided into Group 1, which was the control group (SHR), Group 2, which was a sample 1-administered group (30 ml/day), Group 3, which was a group to which sample 2 diluted two times with distilled water was administered (30 ml/day), and Group 4, which was a pure sample 2-administered group (30 ml/day). Four animals were assigned to each group, and the experiment was performed for three weeks. The samples were orally administered within 30 minutes and, then, fodder and drinking water were freely fed. The experimental groups were as follows:
Group 1: SHR+D.W. (0.6 ml/rat, p.o.)
Group 2: SHR+Sample 1 (0.6 ml/rat, p.o.)
Group 3: SHR+Sample 2 (0.6 ml/rat, p.o.)
Group 4: SHR+betanin (50 mg/kg, p.o.)

The blood pressure was measured using CODA non-invasive blood pressure system (Kent Scientific, Torrington, Conn.). The temperature of the experimental animal's tail before blood pressure measurement was maintained at 32° C. to 35° C., and blood pressure measurement was performed in the stabilized state.

Figure 8:
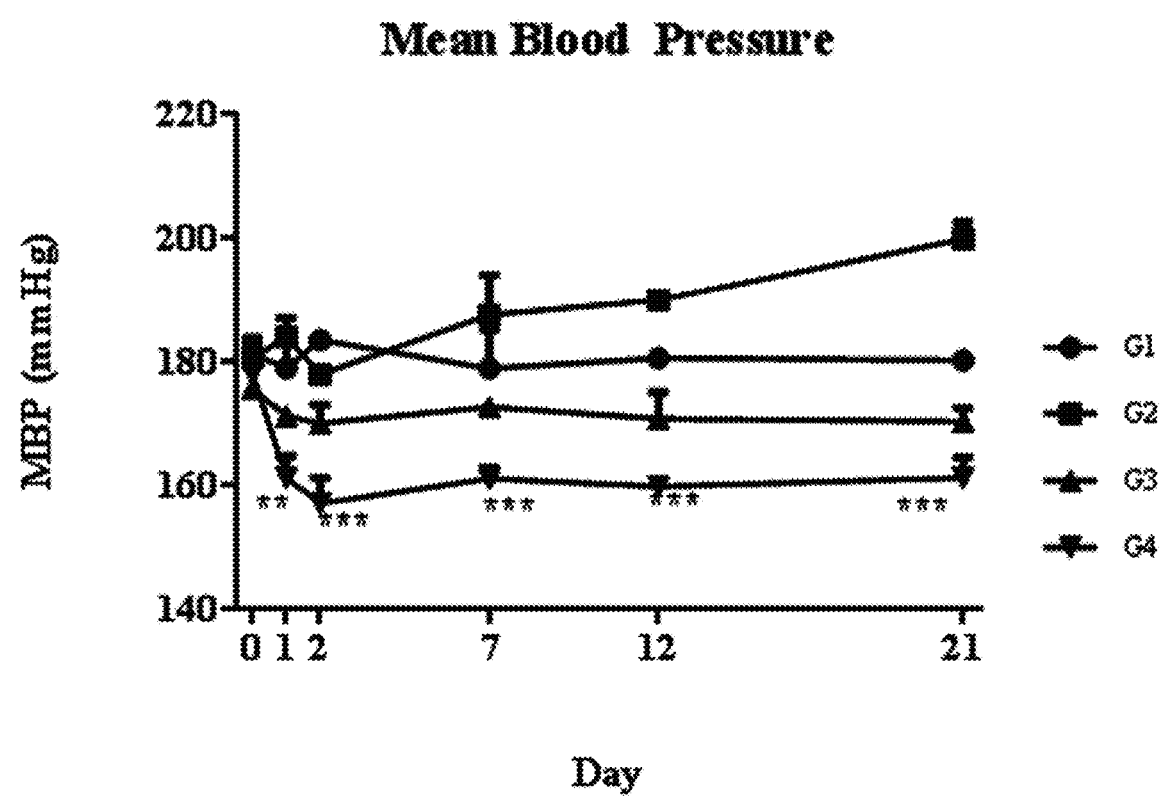
FIG. 8 is a graph illustrating variations in blood pressure after a beet juice manufactured according to the present invention is repeatedly administered in an animal experiment.

The results are shown as in FIG. 8 (FIG. 8). The sample 1-administered group (G1) showed steady increases in blood pressure two days after. The sample 2-administered group showed blood pressure drops in proportion to the amount of sample 2 administered (G3, G4).

As such, from the results of one-time or repeated administration, it can be shown that sample 2 has the effect of mitigating high blood pressure.

<8-4> Measure Flaccid Reactivity of Extracted Blood Vessels

To inspect the flaccidity of blood vessels, the thoracic aorta was extracted and formed into aortic rings which were then suspended in an organ bath filled with Krebs solution (in mM, NaCl 120, KCl 4.75, Glucose 6.4, $NaHCO_3$ 25, $KH_2PO_4$ 1.2, $MgSO_4$ 1.2, $CaCl_2$ 1.7), While the experiment proceeds, the temperature was maintained at 37° C., and the pH of the solution was maintained at 7.4 by supplying carbogen (95% $O_2$, 5% $CO_2$). After the resting tension of the aortic was adjusted to 1.5 g, the solution was replaced every 20 minutes so as to provide stabilization for one hour. The contraction and relaxation of blood vessels were recorded by the physiograph recorder (PowerLab/400, AD instruments U.S.A.) and analyzed in the Chart8 program, with the other end of the fixed aortic ring connected to the isometric force-displacement transducer (FT03, Grass, AD instruments, U.S.A.). In an endothelial derived relaxing experiment, endothelial cell-robust blood vessels were treated with $10^{-6}$M phenylephrine (PE) to contract the blood vessels, and the relaxation reaction was observed with a concentration ($10^{-9}$ M to $10^{-4}$M) of acetylcholine (Ach) cumulatively applied, and $pD_2$ (–Log $EC_{50}$) was calculated.

Figure 9:
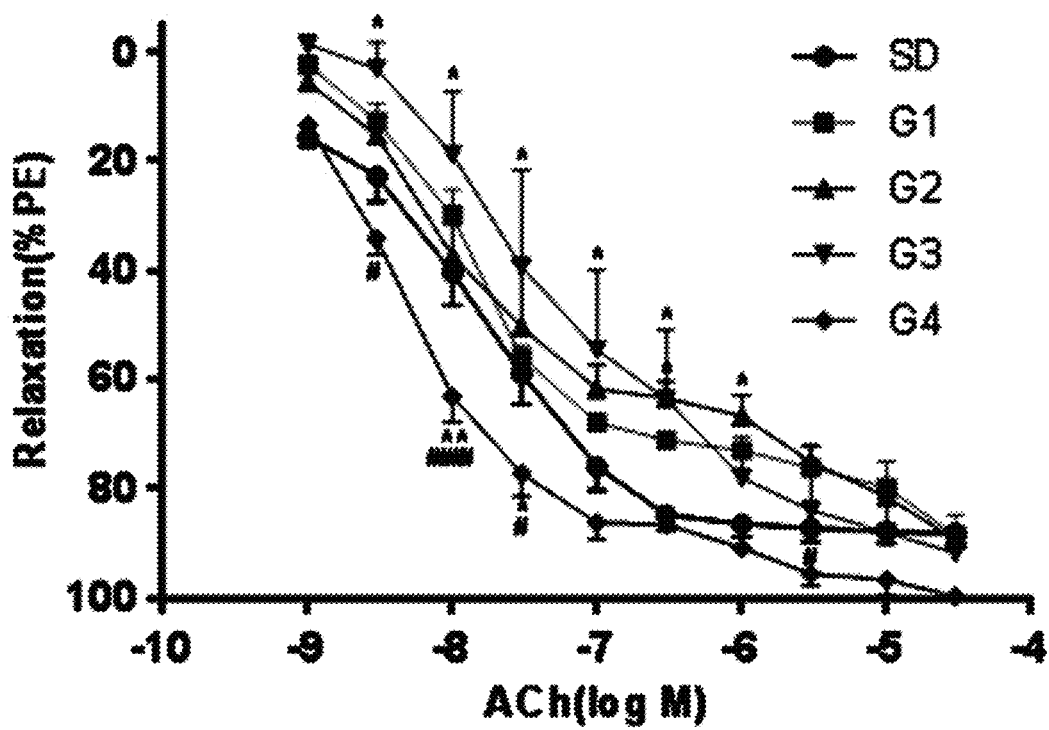
FIG. 9 is a graph illustrating the flaccidity of extracted blood vessels in an animal experiment on a beet juice manufactured according to the present invention.

As a result, as shown in FIG. 9 and Table 4, the SHR showed a reduction in reactivity to Ach, i.e., relaxation, as compared with the normal blood pressure groups (SD) and, although no significant difference was made between the groups in light of EC50, the sample 2-administered group (G4) showed an increase in blood vessel relaxation as compared with the other groups (Table 4 and FIG. 9).

TABLE 4

| Group | $EC_{50}(\mu M)$ | $pD_2$ |
|---|---|---|
| SD | 0.0506 ± 0.0141 | 7.3772 ± 0.1411 |
| G1 | 1.4620 ± 1.2039 | 6.4521 ± 0.4849 |
| G2 | 0.4715 ± 0.0740 | 6.3366 ± 0.0653 |
| G3 | 0.1525 ± 0.0758 | 7.2441 ± 0.5980 |
| G4 | 0.0117 ± 0.0023 | 7.9514 ± 0.0946 |

<8-5> Measure Variations in Weight of Organ

On the final day of the experiment, all of the experimental animals were sacrificed by $CO_2$ gas, and blood was collected through the abdominal veins and the hearts, livers, kidneys, and brains were extracted. To figure out variations in the weight of organs, each organ was extracted and weighed, and the weight of organ was divided by the body weight of the experimental animal, and the resultant values were compared.

Organ weight index=organ weight/body weight×100(%)

Figure 10:
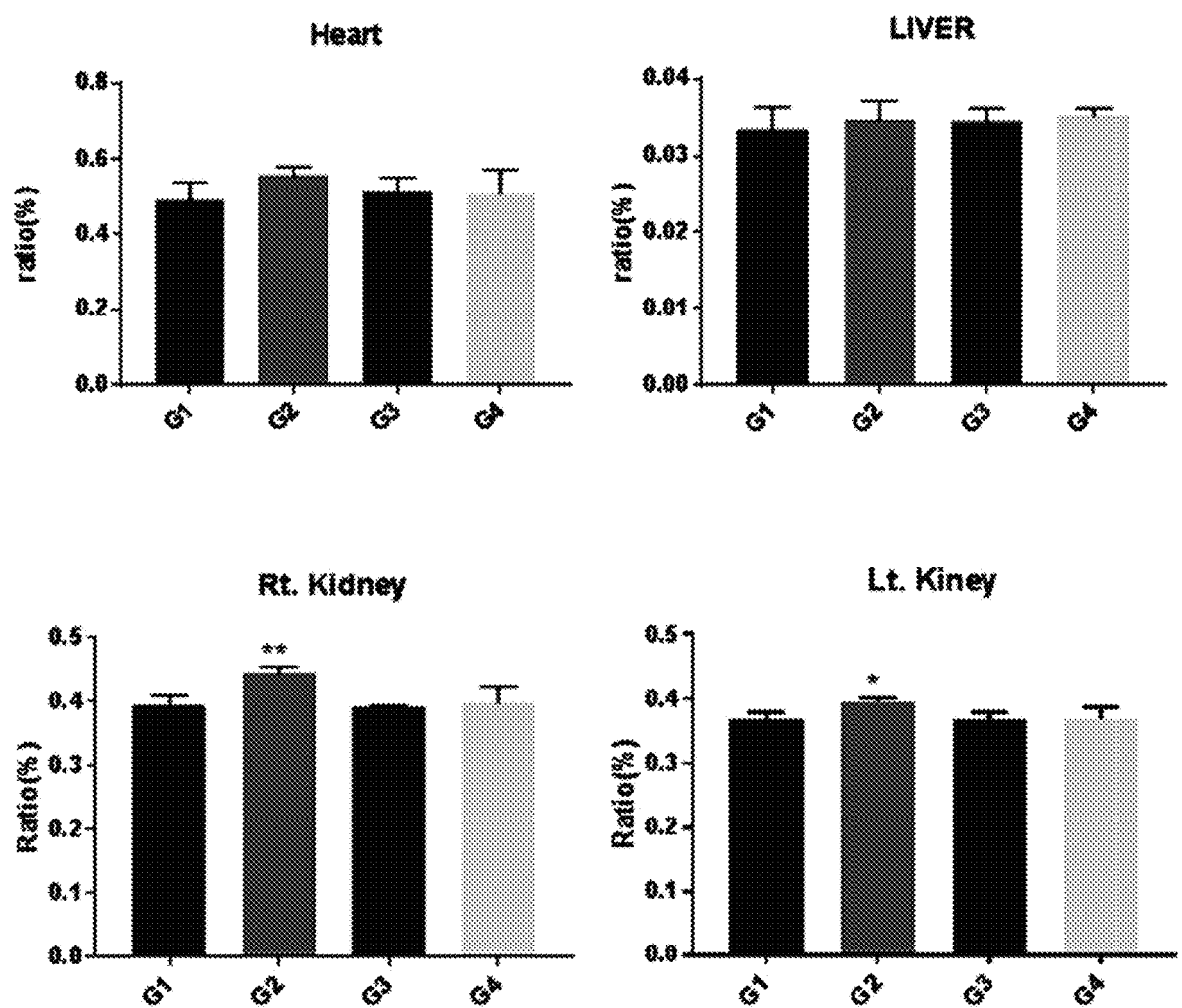
FIG. 10 is a graph illustrating variations in the weight of an organ in an animal experiment on a beet juice manufactured according to the present invention.

As a result, as shown in FIG. 10, no difference was shown between the groups in light of the variation in body weight due to administration of the samples. No difference in the organ weight for the body weight was observed between the sample 2-administered group and the control group. However, the sample 1-administered group showed significant increases in both the right and left kidneys (FIG. 10).

<8-6> Measure Variations in Blood Nitrite

The concentration of nitrite in serum was measured by, e.g., the Miranda method. A volume of ethanol which is two times the volume of serum was applied to the serum and then centrifuged at 3,000 rpm for 10 minutes to remove proteins.

The same amount of vanadium (III) chloride was added to 100 µl of the supernatant liquid to convert nitrate into nitrite. Thereafter, 50 µl of Griess reagent sulfanilamide and 50 µl of N-(1-naphthyl) ethylenediamine were added and left for reaction at 37° C. for three hours, and then the absorbance at 570 nm was measured.

Figure 11:
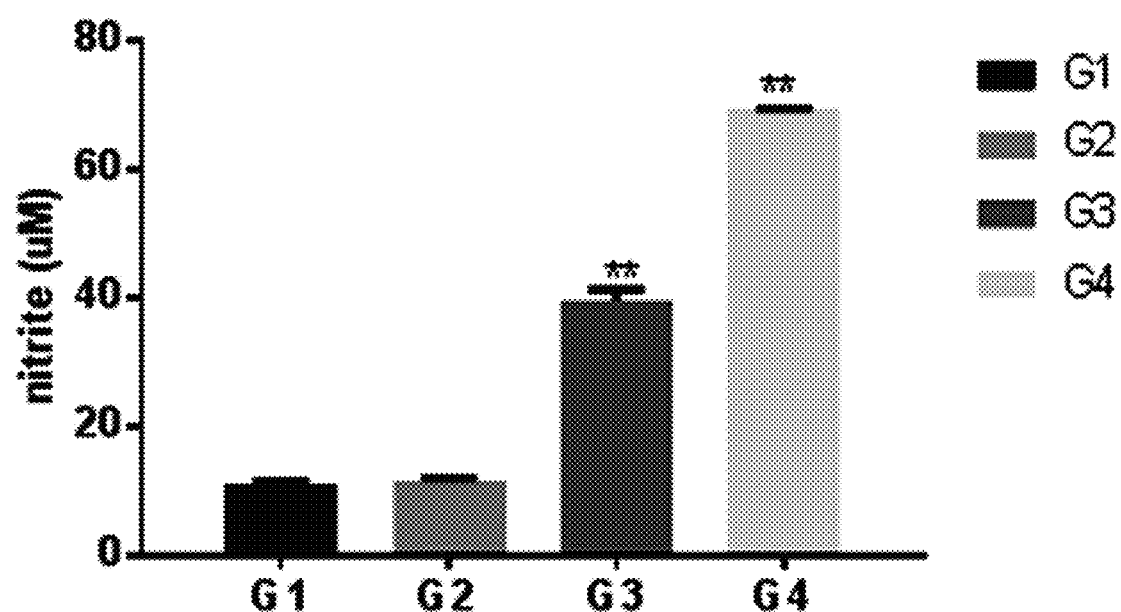
FIG. 11 is a graph illustrating variations in blood nitrite in an animal experiment on a beet juice manufactured according to the present invention.

As a result, as shown in FIG. 11, blood nitrite was increased dose-dependently in the sample 2-administered groups (G3 and G4), but no significant difference was shown between the sample 1-administered group and the control group. The blood nitrite concentration was 11.0±0.7, 11.6±0.6, 39.7±1.6, and 69.2±0.3 µM in G1, G2, G3, and G4, respectively (FIG. 11).

<8-7> Measure Lipid Peroxidation Index

The content of MDA in serum was measured using EZ-Lipid peroxidation (TBARS) assay kit (DoGenBio, Seoul). 35 mg of TCA was added to the serum and was centrifuged. Then the supernatant liquid was taken. 200 µl of indicator was added to 200 µl of supernatant liquid and was then left for reaction at 65° C. for 45 minutes. Then, the absorbance at 540 nm was measured.

Figure 12:
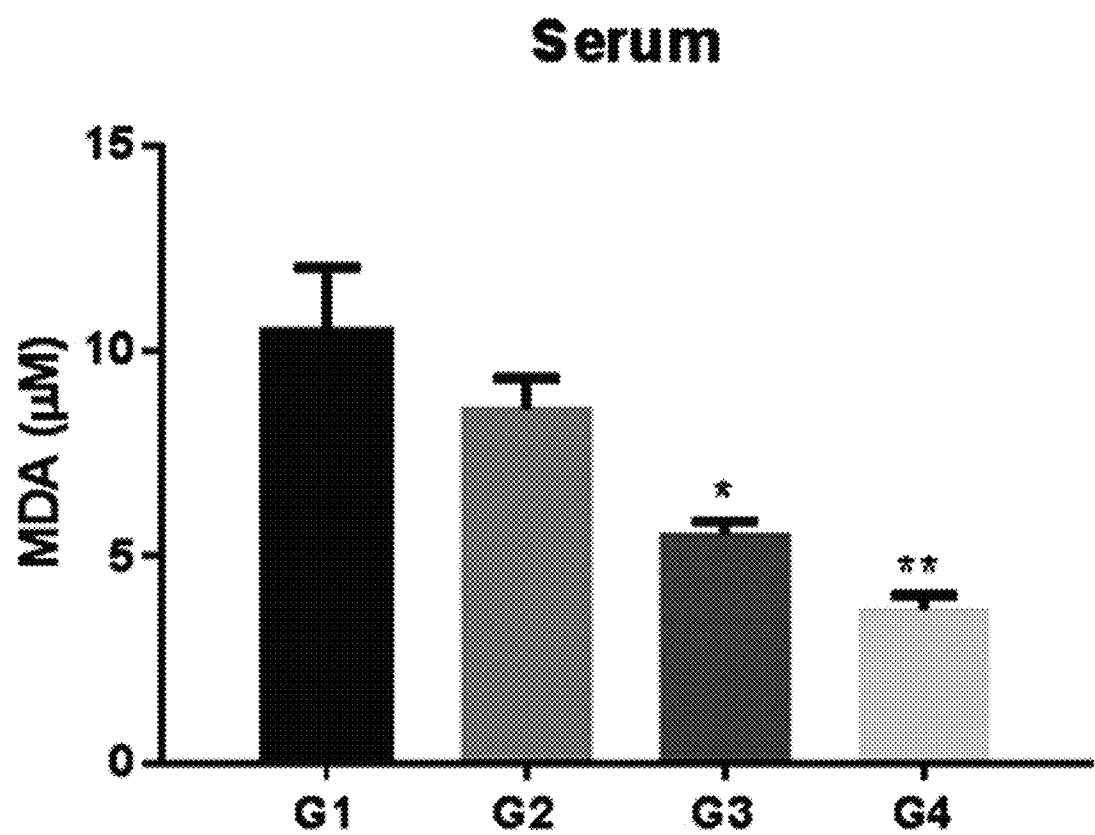
FIG. 12 is a graph illustrating variations in MDA which is an index of blood lipid oxidation in an animal experiment on a beet juice manufactured according to the present invention.

As a result, as shown in FIG. 12, the concentration of MDA in blood, which is an index for lipid oxidation, made no difference between the sample 1-administered group (G1) and the control group but, as the dose of sample 2 administered increase, it was reduced significantly. The concentration of MDA in blood was 9.8±1.8 for G1, 8.6±0.7 for G2, 5.6±0.3 for G3, and 3.8±0.4 µM for G4, and sample 2 showed the effect of significant protection against lipid peroxidation (FIG. 12).

As a result, when orally administered to hypertensive animals, sample 2, presented significant blood pressure drops, increases in nitrite in blood, and reductions in MBA, but no significant variations in weight and organ index. Further, blood vessel reactivity to acetylcholine was enhanced.

In contrast, when sample 1 was orally administered to hypertensive animals, no blood pressure drops were observed but blood pressure was rather elevated. Further, the kidney weight was increased.

From these results, it is identified that while sample 1 does not provide the effect of dropping blood pressure, sample 2 enhances blood vessel reactivity via increases in in-blood nitrogenous compounds and suppression of lipid peroxidation. Thus, it can be shown that the beet juice of the present invention may deliver superior effects of mitigating hypertension.

The invention claimed is:

1. A healthy food, comprising a low temperature-ripen beet juice, a carrot juice, and an apple juice, wherein the low temperature-ripen beet juice is obtained by baking the peeled beet at a temperature ranging from 200° C. to 300° C. for 30 seconds to one minute, juicing the baked beet, and low-temperature ripening the juiced beet at a temperature ranging from 0° C. to 10° C. for three days to four days, and wherein the low temperature-ripen beet juice, the carrot juice, and the apple juice are mixed in a weight ratio of 2.0 to 3.0:1.5 to 2.5:5.0 to 6.0 to increase in-blood nitrogenous compounds, have high blood vessel reactivity, and suppression of lipid peroxidation.

2. The healthy food of claim 1, wherein the healthy food is an anti-oxidative healthy food.

3. The healthy food of claim 1, wherein the healthy food is an anti-hypertensive healthy food.

* * * * *